US00PP33663P3

(12) United States Plant Patent
Growns

(10) Patent No.: US PP33,663 P3
(45) Date of Patent: Nov. 23, 2021

(54) ***GREVILLEA* PLANT NAMED 'GR85'**

(50) Latin Name: ***Grevillea* hybrid**
Varietal Denomination: GR85

(71) Applicant: Botanic Gardens and Parks Authority, Perth (AU)

(72) Inventor: Digby James Growns, Perth (AU)

(73) Assignee: BOTANIC GARDENS AND PARKS AUTHORITY, Perth (AU)

( * ) Notice: Subject to any disclaimer, the term of this patent is extended or adjusted under 35 U.S.C. 154(b) by 0 days.

(21) Appl. No.: 16/873,524

(22) Filed: Apr. 29, 2020

(65) Prior Publication Data

US 2021/0329822 P1 Oct. 21, 2021

(30) Foreign Application Priority Data

Apr. 30, 2019 (AU) ..... 2019/058

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

(56) References Cited

U.S. PATENT DOCUMENTS

PP18,035 P3 9/2007 Cox et al.

OTHER PUBLICATIONS

UPOV hit on *Grevillea* plant named, 'GR85', QZ PBR 2019058, accepted Apr. 30, 2019.*
UPOV hit on *Grevillea* hybrid plant named, 'GR86', filed Apr. 6, 2019, AU PBR 2019058.*
UPOV hit on *Grevillea* plant named, 'GR85', AU PBR 2019058, filed Apr. 6, 2019.*

* cited by examiner

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of *Grevillea* Plant, herein referred to by its cultivar name, 'GR85', is provided which forms attractive, bicolor flowers which are creamy yellow turning apricot. Grey-green colored foliage is formed. The vegetation is moderately vigorous, and the growth habit is mounding and compact. The new variety is particularly well suited for providing distinctive ornamentation in the landscape.

1 Drawing Sheet

Botanical/commercial classification:
Latin name: *Grevillea* hybrid.
Varietal denomination: 'GR85'.

SUMMARY OF THE INVENTION

The new variety of *Grevillea* plant, botanically known as *Grevillea* hybrid, of the present invention originated by cross pollination in Perth, Western Australia, wherein two parents were crossed which previously had been studied in the hope that they would contribute the desired characteristics. The female parent (i.e., the seed parent) was the '20101113" variety (not patented). The male parent (i.e., the pollen parent) was the '20091832' variety (not patented).

The parentage can be summarized as follows:

'20101113' x '20091832'

The new cultivar was discovered and selected as a single flowering plant within the progeny of the above stated cross pollination during March 2012 in a controlled environment in Perth, Western Australia.

It was found that the new variety of *Grevillea* plant of the present invention possesses the following combination of characteristics:

(a) forms bicolor flowers, which are creamy yellow turning apricot,
(b) exhibits grey-green colored foliage,
(c) provides moderately vigorous vegetation, and
(d) forms mounding and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the '20101113' variety (i.e., the seed parent) displays toothbrush shaped, single colored flowers, which are red, whereas the new variety displays cylindrical shaped bicolor flowers, which are creamy yellow turning apricot. The '20091832' variety (i.e., the pollen parent) displays single colored flowers, which are white, exhibits green colored foliage, and forms an upright shrub growth habit, whereas the new variety displays bicolor flowers, which are creamy yellow turning apricot, exhibits grey-green colored foliage, and forms mounding and compact growth habit. Moreover, the new variety can be readily distinguished from other similar non-parental varieties. For example, the 'Peaches and Cream' variety (U.S. Plant Pat.

No. 18,035) exhibits green colored foliage, whereas the new variety exhibits grey-green colored foliage.

The new variety has been found to undergo asexual propagation in Perth, Western Australia by terminal stem cuttings since March 2012. Asexual propagation by terminal stem cuttings in Perth, Western Australia has shown that the characteristics of the new variety are homogeneous, stable, and strictly transmissible by such asexual propagation from one generation to another. Accordingly, the new variety undergoes asexual propagation in a true-to-type manner.

The new variety has been named 'GR85'.

BRIEF DESCRIPTION OF THE PHOTOGRAPHS

The accompanying photographs show, as nearly true as it is reasonably possible to make the same in color illustrations of this character, typical specimen of the new variety. Colors in the photographs differ slightly from the color designations cited in the detailed description, which accurately describes the colors of the new variety.

The Drawing—illustrates specimens of the inflorescence—close-up view.

DETAILED BOTANICAL DESCRIPTION

The chart used in the identification of colors described herein is that of The Royal Horticultural Society (R.H.S. Colour Chart), London, England, 1995 edition, except where general color terms of ordinary significance are used. The terminology which precedes reference to the chart has been added to indicate the corresponding color in more common terms. The color values were determined in February 2021 under natural light conditions in Folsom, Calif.

The following descriptions and measurements describe plants produced from cuttings from stock plants. The plants were grown outdoors in Folsom, Calif. Measurements and numerical values represent averages of typical plants.

Botanical classification: *Grevillea* hybrid 'GR85'.

Parentage:

*Female parent*.—Proprietary breeding seedling, *Grevillea* '20101113', not patented.

*Male parent*.—Proprietary breeding seedling, *Grevillea* '20091832', not patented.

PROPAGATION:

*Type cutting*.—Terminal stem cuttings.

*Root description*.—Light brown in color, fine.

*Rooting habit*.—Freely branching, tight groupings of small rootlets.

Plant:

*Growth habit and general appearance*.—Moderately vigorous, mounding, and compact growth habit.

*Hardiness*.—USDA Zone 8 through 11.

*Disease and pest resistance*.—Resistance to pathogens and pests common to *Grevillea* has not been observed.

*Size*.—Height: Approximately 1.5 to 2.0 meters. Width: Approximately 2.5 to 3.0 meters.

*Branching habit*.—Freely branching.

*Branch*.—Strength: Strong. Quantity: One to two main branches. Length to base of peduncle: Approximately 14.0 cm. Diameter: Approximately 4.0 cm. Length of central internode: Approximately 3.0 cm. Texture: Tomentose. Attitude of the main stem to horizontal: Oblique. Cross-sectional stem shape: Elliptical. Lateral branch aspect in terms of degrees from the main stem: 60 to 90 degrees from stem. Cross-section of lateral branches: Round. Color of young stems: commonly near Greyed-Green Group 195B. Color of mature stems: commonly near Greyed-White Group 156A.

Foliage:

*General description*.—Form: Simple. Arrangement: Alternate. Fragrance: None detected. Density: Moderately bushy.

*Leaves*.—Aspect: Acute angle to stem. Margin: Entire, pinnatisect. Undulation of leaf margin: Leaf margins curve downwards covering the lower leaf. Apex of lobes: Acute. Base: Narrowly attenuate. Leaf blade shape: 6 to 10 lobed, lobes are linear and accumulated toward the apex. Profile of leaf cross section: Lenticular. Venation pattern: Pinnate. Length of mature leaf: Approximately 22.0 to 23.0 cm. Width of mature leaf: Approximately 8.0 to 9.0 cm. Texture of upper surface: Immature leaves pubescent, becoming smooth with maturity. Texture of lower surface: Slightly tomentose. Pubescence color: commonly near Greyed-White Group 156D. Color of upper surface of young foliage: commonly near Greyed-Yellow Group 162B. Color of lower surface of young foliage: commonly near Greyed-Orange Group 163B. Color of upper surface of mature foliage: commonly near Green Group 138A. Color of lower surface of mature foliage: commonly near Yellow-Green Group 148D, indistinguishable venation.

*Petiole*.—Length: Approximately 4.0 to 6.0 cm. Width: Approximately 1.0 to 2.0 mm. Texture: Appears smooth. Color: commonly near Green Group 138B.

*Stipule*.—Arrangement: Dorsal node only. Texture: Pubescent brown orange. Shape: Linear. Length: Approximately 1.0 to 2.0 cm. Width: Approximately 1.0 mm.

Flower:

*Flowering habit*.—Freely flowering habit under outdoor growing conditions with substantially continuous blooming.

*Lastingness of individual inflorescence on the plant*.—Approximately 2 to 2.5 weeks.

*Sequence of flower opening*.—Acropetal.

*Color*.—Upon opening: commonly near Red Group 44B. When fully opened: commonly near Orange-Red Group N34A. When fading: commonly near Orange-Red Group 33D.

Inflorescence:

*General description*.—Type: Raceme. Self-cleaning. Shape: Secund conflorescence. Aspect: Facing upwards and outward. Arrangement: Terminal and from leaf axils. Attitude of tepal limb in relation to the longitudinal axis of the flower bud: Upright. Fragrance: none detected. Quantity per plant: Approximately 5 to 10 flowers at a time. Inflorescence Diameter: Approximately: 8.0 cm. Inflorescence Depth: Approximately 12.0 cm.

*Bud*.—Rate of opening: Generally, takes 6 to 8 days for bud to progress from first color to fully open floret.

*Bud just before opening*.—Shape: Globular. Diameter: Approximately 3.5 mm. Texture of outer surface: Tomentose. Pubescence color: commonly near Greyed-Yellow Group N161A. Color: commonly near Greyed-Green Group 194B.

*Florets*.—Quantity per inflorescence: Approximately 120 to 130. Arrangement: Primarily in pairs. Length: Approximately 3.0 mm. Diameter: Approximately 7.0 mm.

*Perianth*.—Shape: Tubular with a ventral limb, becomes revolute during anthesis. Length: Approximately 10.0 mm. Diameter at widest point: Approximately 7.0 mm. Diameter as base: Approximately 4.0 mm. Color on the bud: commonly near White Group 155C. Hairiness of perianth: Slightly pubescent. Perianth coherence of tepals on the dorsal side: One third to two thirds.

*Tepals*.—Quantity: 4. Shape: Linear. Margin: Entire. Apex: Acute. Length: Approximately 10.0 mm. Width: Approximately 3.0 mm. Texture of outer surface: Tomentose. Texture of inner surface: Glabrous. Color of outer surface when fully open: commonly near Green-Yellow Group 1C. Color of inner surface when fully open: commonly near Red Group 38B.

*Peduncle*.—Strength: Strong. Aspect: Erect. Length: Approximately 1.5 cm. Diameter: Approximately 2.0 to 2.5 cm. Texture: Tomentose. Color: commonly near Yellow-Green Group 144D.

*Rachis*.—Strength: Strong. Length: Approximately 9.0 to 10.0 cm. Diameter: Approximately 3.0 mm. Texture of outer surface: Tomentose. Color: commonly near Yellow-Green Group 144A.

*Pedicel*.—Strength: Strong. Aspect: Erect. Length: Approximately 1.0 mm. Diameter: Approximately 2.0 mm. Texture of outer surface: Tomentose. Pubescence color: commonly near Yellow-Green Group N154C. Color: commonly near Yellow-Green Group 146D.

*Reproductive organs*.—Androecium: Anthers located within perianth limb and basally attached to perianth. Anther quantity: 4 per floret. Anther Shape: Bilobed. Anther length: Approximately 1.0 mm. Anther color: commonly near Greyed-Orange Group 164C. Pollen amount: Sparse. Pollen color: commonly near Greyed-Orange Group 163A. Attitude of pollen presenter to style: Lateral. Gynoecium: Stigma functions as a pollen presenter holding pollen for pollinators to remove until stigma matures becoming receptive to cross pollination. Nectary located at base of ovary. Pistil quantity: 1 per flower. Pistil length: Approximately 3.0 cm. Stigma shape: Funnel. Stigma length: Approximately 1.0 mm. Stigma color: commonly near Greyed-Yellow Group 160D. Style length: Approximately 3.0 cm. Style color: commonly near Greyed-Yellow Group 161C. Curvature of the style: Curved, eventually erect. Hairiness of the style: Smooth. Distribution of style hair: Not applicable, smooth style. Ovary length: Approximately 1.0 mm. Ovary texture: Tomentose. Pubescence color: commonly near White Group 155A. Ovary color: commonly near Greyed-Yellow Group 162A. Nectary size: Less than 1.0 mm in length and 1.5 mm in width. Nectary color: commonly near Yellow-Green Group 145C.

*Seed and fruit production*.—Neither seed nor fruit production has been observed.

Plants of the 'GR85' variety have not been observed under all possible environmental conditions to date. Accordingly, it is possible that the phenotypic expression may vary somewhat with changes in light intensity and duration, cultural practices, and other environmental conditions, without, however, any variance in genotype.

I claim:

1. A new and distinct *Grevillea* Plant characterized by the following combination of characteristics:

(a) forms bicolor flowers, which are creamy yellow turning apricot, (b) exhibits grey-green colored foliage, (c) provides moderately vigorous vegetation, and (d) forms mounding and compact growth habit;

substantially as herein shown and described.

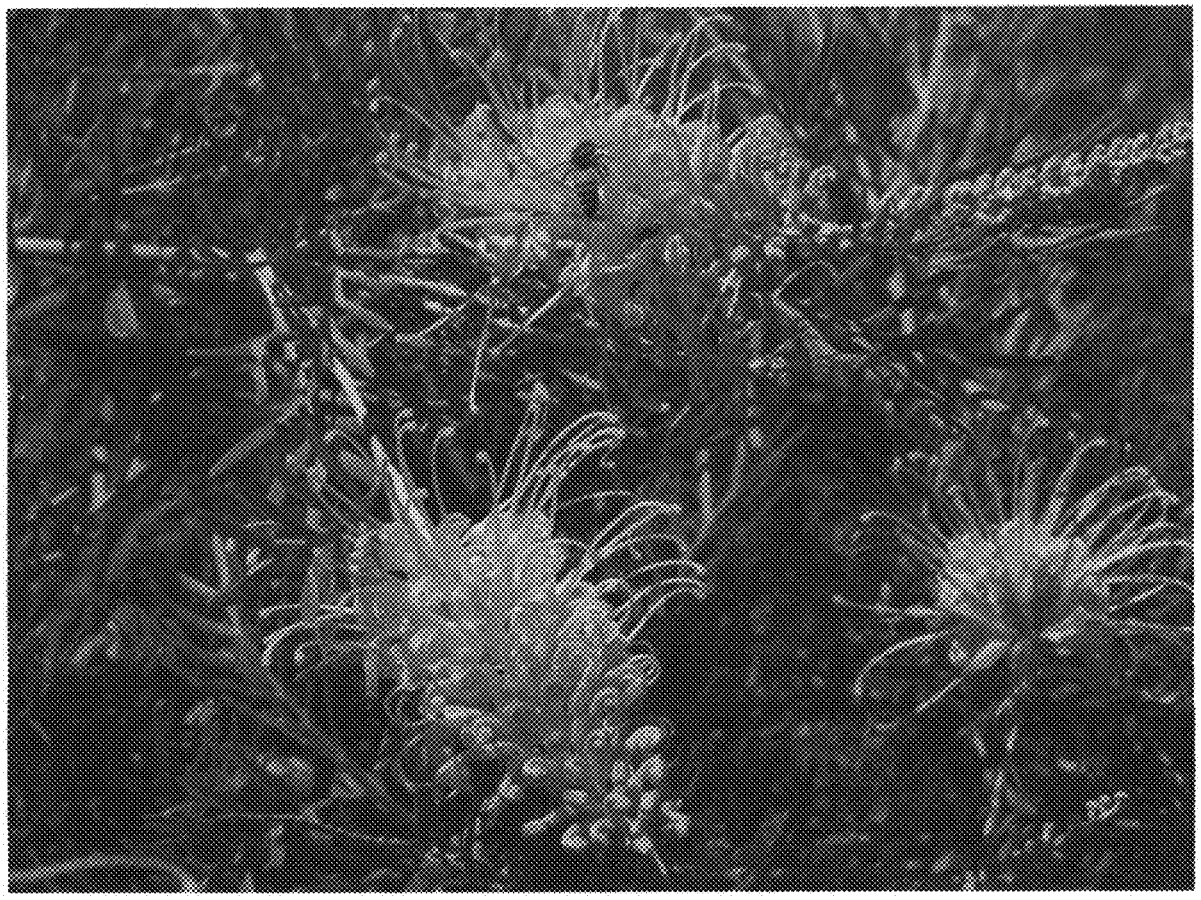

* * * * *